United States Patent [19]

Mahaffey et al.

[11] Patent Number: 5,506,142
[45] Date of Patent: Apr. 9, 1996

[54] PROBE WASH FOR LIQUID ANALYSIS APPARATUS

[75] Inventors: Richard C. Mahaffey, Laguna Niguel; John C. Mazza, El Toro; Ronald N. Diamond, Anaheim Hills, all of Calif.

[73] Assignee: Dade International Inc., Deerfield, Ill.

[21] Appl. No.: 301,522

[22] Filed: Sep. 7, 1994

Related U.S. Application Data

[63] Continuation of Ser. No. 807,161, Dec. 13, 1991, abandoned.

[51] Int. Cl.⁶ .................................................. B01L 3/02
[52] U.S. Cl. ........................... 436/49; 436/52; 436/53; 436/54; 436/79; 436/180; 422/100; 422/103; 422/63; 73/864.22; 73/864.23; 73/864.24; 73/864.25; 73/864.12; 73/864.15
[58] Field of Search ................. 73/864.22, 864.23, 73/864.24, 864.25, 864.12, 864.15; 422/103, 100, 63; 436/49, 54, 79, 180, 52, 53

[56] References Cited

U.S. PATENT DOCUMENTS

| | | | |
|---|---|---|---|
| 2,899,280 | 8/1959 | Whitehead et al. | 436/53 |
| 3,134,263 | 5/1964 | DeJong | 422/63 |
| 3,241,432 | 3/1966 | Skeggs | 422/63 |
| 3,241,923 | 3/1966 | Ferrari | 422/63 |
| 3,266,322 | 8/1966 | Negersmith et al. | 73/864.22 |
| 3,282,651 | 11/1966 | Ferrari et al. | 436/54 |
| 3,484,170 | 4/1966 | Smythe et al. | 436/53 |
| 3,572,994 | 3/1971 | Hochstrosser | 436/53 |
| 3,654,959 | 4/1972 | Kassel | 436/53 |
| 3,666,420 | 5/1972 | Paatzsch | 23/253 R |
| 3,719,086 | 3/1973 | Bannister et al. | 73/864.22 |
| 3,872,730 | 3/1975 | Ringrose et al. | |
| 3,912,456 | 10/1975 | Young | |
| 3,960,020 | 6/1976 | Gordon et al. | 73/864.22 |
| 3,976,429 | 8/1976 | Ginsberg | 73/864.22 |
| 3,990,312 | 11/1976 | Koukol | 73/864.15 |
| 4,000,973 | 1/1977 | Petersen | 436/53 |
| 4,015,938 | 4/1977 | Jay | 436/53 |
| 4,076,503 | 2/1978 | Atwood et al. | |
| 4,131,426 | 12/1978 | Range | 141/1 |
| 4,148,859 | 4/1979 | Simpson et al. | 73/864.22 |
| 4,245,509 | 1/1981 | Mody et al. | 73/863.86 |
| 4,283,262 | 8/1981 | Cormier et al. | 204/411 |
| 4,434,672 | 3/1984 | Williamson et al. | 73/864.22 |
| 4,456,037 | 6/1984 | Gocho | 141/1 |
| 4,528,159 | 7/1985 | Liston | 422/65 |
| 4,543,238 | 9/1985 | Mimura et al. | 422/63 |
| 4,635,665 | 1/1987 | Namba et al. | 422/100 |

(List continued on next page.)

FOREIGN PATENT DOCUMENTS

| | | |
|---|---|---|
| 0355791 | 2/1990 | European Pat. Off. |
| 0426986 | 5/1991 | European Pat. Off. |
| 2547843 | 4/1977 | Germany |
| 3839896 | 6/1989 | Germany |
| 242858 | 10/1987 | Japan ........................ 436/49 |
| 2126117 | 3/1984 | United Kingdom |
| WO8810158 | 12/1988 | WIPO |

OTHER PUBLICATIONS

International Search Report By European Patent Office Dated Mar. 22, 1993.

Primary Examiner—James C. Housel
Assistant Examiner—Sharidan Carrillo
Attorney, Agent, or Firm—Joseph P. Reagen; Tilton, Fallon, Lungmus & Chestnut

[57] ABSTRACT

A system for cleaning a probe used in analytic equipment—for example, that used in analysis of body fluids—in order to reduce carry-over of materials from one sample to the next. A probe wash is provided in which the simultaneous introduction of pressurized air and water creates a turbulent flow including the use of a pressurized gas stream of short duration to blow the residue of the previous sample out of the probe prior to washing with additional diluent liquid. Also, a waste receptacle is provided which uses a filtered air vent and a liquid saturated material around the probe receiving opening to prevent the escape of aerosols from the receptacle.

13 Claims, 2 Drawing Sheets

U.S. PATENT DOCUMENTS

| | | | |
|---|---|---|---|
| 4,756,201 | 7/1988 | Uffenheimer | 73/864.83 |
| 4,815,978 | 3/1989 | Mazza et al. | 422/63 |
| 4,865,993 | 9/1989 | Cassaday | 436/52 |
| 4,871,682 | 10/1989 | Mazza | 422/100 |
| 4,871,683 | 10/1989 | Harris et al. | 436/531 |
| 4,900,933 | 2/1990 | Nestor et al. | |
| 4,948,563 | 8/1990 | Kanewshe | 422/63 |
| 4,951,512 | 8/1990 | Mazza et al. | 422/66 |

PROBE WASH FOR LIQUID ANALYSIS APPARATUS

This is a continuation of application Ser. No. 07/807,161, filed on Dec. 13, 1991, now abandoned.

FIELD OF THE INVENTION

The present invention relates to liquid sample analysis apparatus which uses a sampling probe to deliver liquids from a sample container to the analysis equipment. More particularly, the invention relates to an improved system for cleaning of the probe between samples in order to reduce carry-over of materials from one sample to the next.

BACKGROUND ART

Various systems are available for the analysis of liquids, for example, body liquids which need to be quantitatively analyzed with respect to specific ingredients. One such system known as the Paramax Analytic System is fully shown and fully described in U.S. Pat. No. 4,528,159 (Liston) issued Jul. 9, 1985. Such analysis systems generally include a probe which enters the sample container, such as a test tube, either through the open top thereof or by temporarily entering through the closure, for example, by puncturing a rubber stopper to form a temporary opening. See, for example, U.S. Pat. No. 4,951,512 (Mazza et al.) issued Aug. 28, 1990.

Reusable probes that are used to deliver aliquots from successive containers such as blood collection tubes or liquid reagent vessels are a source of intra-sample carryover or contamination. In order to minimize contamination and carry-over between samples, it has been conventional to flush the probe with a diluent liquid such as water, for example, as described in the Liston patent. Another technique shown, for example, in U.S. Pat. No. 3,266,322 (Negersmith et al.) issued Aug. 16, 1966, has entailed aspiration of air through the probe by means of a vacuum pump or the aspirating pump used to withdraw the sample liquid from the sample container. Such aspiration, however, introduces the possibility of drawing the unwanted carry-over contaminants deeper into the tubing and apparatus which comprises the sampling system. It has also been proposed to utilize a separate probe wash sleeve through which a pressurized rinse liquid is flushed. See for example U.S. Pat. No. 4,756,201 (Uffenheimer) granted Jul. 12, 1988. In light of these existing probe wash systems, a need has continued to exist for an improved method and apparatus for effectively cleaning such probes.

SUMMARY OF THE INVENTION

The principal object of the invention is to provide a new probe wash system that substantially reduces carryover between samples aspirated by the probe. An important aspect of the invention is to provide a probe wash in which a turbulent flow is created in the probe by means of a simultaneous introduction of pressurized air and water. Alternatively such turbulent flow is created by introduction of bursts of the air and water in rapid sequence. A related aspect of the invention involves the use of a pressurized gas stream of short duration to blow the residue of the previous sample out of the probe prior to washing with additional diluent liquid.

The probe wash system further provides a segmented stream of air and water (or other gas and liquid) that effects thorough cleaning of the probe and its associated flow paths.

An optional aspect of the invention relates to providing a cleaning method in which the air flowpath may be back-flushed with diluent water at the end of the cleaning cycle thereby removing air from the system that could interfere with use of the probe in the next aspiration cycle.

A further aspect of the invention relates to providing a waste receptacle to receive wash liquids from the probe, which receptacle is provided with an inlet opening and, optionally, a vent opening, each of which are provided with means to prevent discharge of aerosols into the atmosphere during the probe washing cycle.

Briefly summarized, the invention provides an improved system for cleaning a probe used for aspirating successive aliquots of liquid from successive containers. The improved means for cleaning said probe between aspiration of the successive aliquots includes a source of diluent liquid such as water which is connected to the probe by means of a first fluid flow path. Means such as a syringe pump is provided for pumping the diluent into the fluid flow path and to the probe. Appropriate control circuitry is provided in order to control the time intervals during which the pump is activated. A source of pressurized gas such as air is connected by a second fluid flow path to the first fluid flow path, at a point intermediate to the probe and the source of diluent liquid. A valve, preferably solenoid controlled, is provided to control the flow of gas to the probe.

In a preferred embodiment of the invention, a waste collection receptacle or chamber is included which is provided with an opening in its top for receiving the probe during the cleaning cycle. This opening is preferably provided with a filament or brush that is saturated with water to prevent the escape of aerosols from the waste receptacle. The chamber is also provided with a filtered outlet for exhaust of gases therefrom, which is important to the proper function of the air purge effected by the invention.

A further aspect of the invention includes means for moving said chamber and said probe relative to each other whereby the probe is inserted through said opening during the cleaning cycle and removed therefrom during a liquid aliquot aspiration cycle. Such motion is provided either by raising of the chamber toward the probe or alternatively by lowering of the probe into the chamber.

Another important aspect of the invention pertains to a method of cleaning a probe, after it has been used to aspirate and dispense a liquid, utilizing the apparatus of the invention. This aspect further contemplates a specific, controlled, rapid sequence of steps. These steps of the wash cycle include (1) opening the wash valve to cause pressurized gas to flow out through the probe, (2) resuming the pumping of diluent while continuing the flow of gas through the probe, (3) closing the valve while continuing the pumping of diluent to re-fill the probe with diluent, and (4) discontinuing the flow of liquid diluent. The probe can then be used for the next liquid aliquot aspiration cycle and the wash cycle repeated thereafter.

BRIEF DESCRIPTION OF THE DRAWINGS

For more complete understanding of the invention reference is made to the embodiment illustrated in greater detail in the accompanying drawings and the following detailed description.

DETAILED DESCRIPTION

Figure 1:
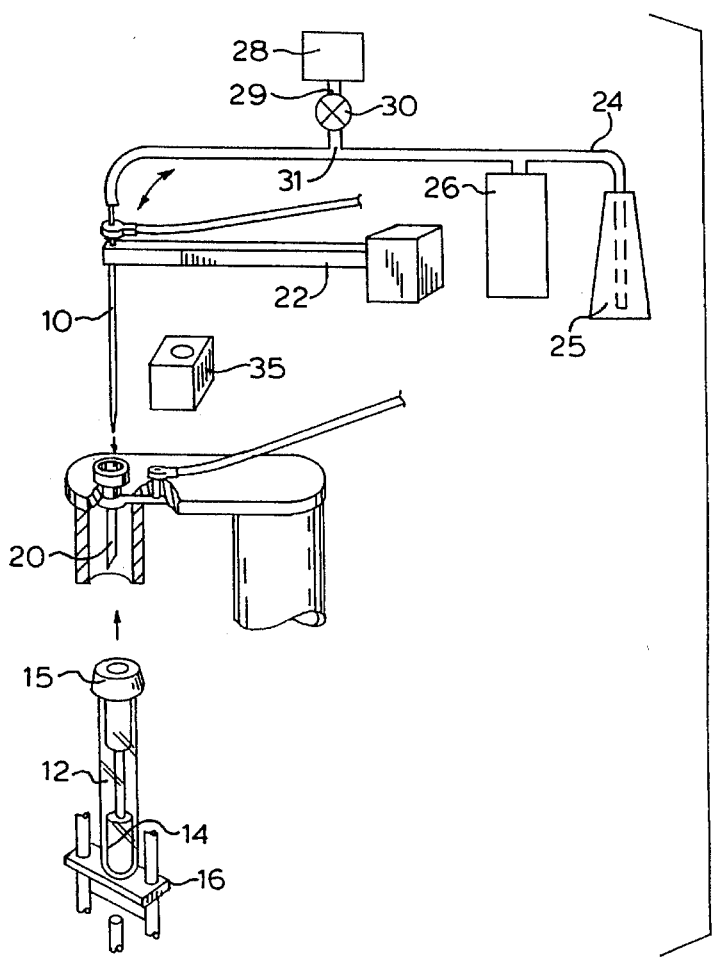
FIG. 1 is a perspective view of a probe of the type used in a liquid sampling system, showing a stoppered container of the type in conjunction with which the probe is typically used and a waste receptacle.

Referring first to FIG. 1 there is seen a probe 10 adapted to enter the interior of a container such as a glass tube 12 which contains a liquid sample 14. Container 12 can be positioned upon a lift platform 16 which is adapted to raise the stoppered container. A puncture tube 20 which includes a non-coring, hollow needle is disposed above container 12 so that it will puncture stoppered end 15 of container 12 when the container is raised. A boom assembly 22 can be provided to lower probe 10 through puncture tube 20 into the interior of container 12 where fluid 14 can be aspirated into probe 10.

As seen in the embodiment of FIG. 1, probe 10 is connected by fluid flow path 24 to a syringe pump 26 (and optionally an additional syringe pump 27, see FIG. 2), which supplies a diluent liquid 25, such as water, to the probe. An air pump 28 is also connected by means of a flow path 29 and T-connection 31 to the fluid flow path 24. A solenoid controlled valve 30 is positioned between air pump 28 and the T-connection 31.

Figure 2:
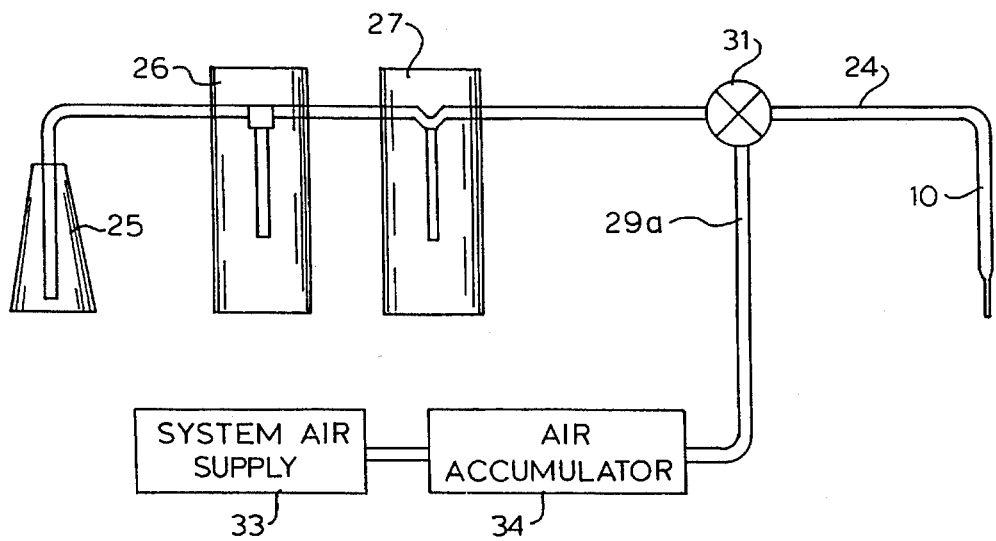
FIG. 2 is a diagrammatic view illustrating a preferred fluid flow path used in conjunction with the invention.

In the alternate embodiment illustrated in FIG. 2, a solenoid-controlled valve 31 is used instead of a separate T-connection, as, with this arrangement, the function of the T-connection is performed by the valve. Fluid flow path 29a is supplied with air from a suitable supply 33, with the pressure and flow rate thereof being controlled by means of an air accumulator 34.

Figure 3:
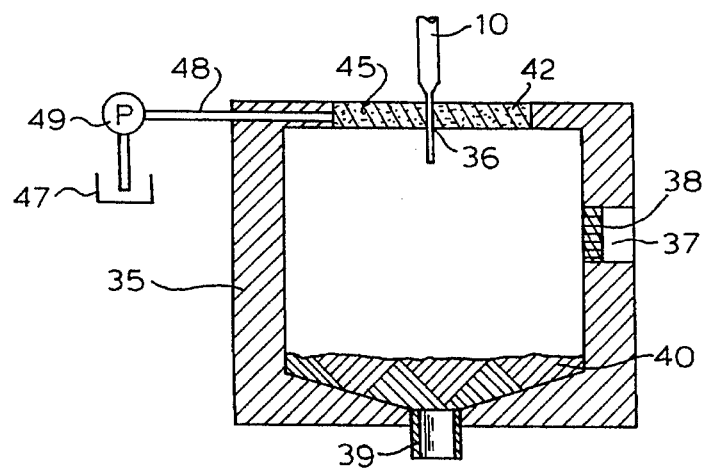
FIG. 3 is a diagrammatic cross-sectional view illustrating a probe of the invention in conjunction with a waste collection chamber.

A waste receiving container 35 is positioned at a location such that the probe 10 can be pivoted thereover and lowered therein through a probe receiving opening 36. Waste receptacle 35, best seen in FIG. 3, is preferably provided with air venting opening 37, which is provided with a hydrophobic air filter 38 to minimize escape of atomized liquids into the atmosphere, while permitting free escape of air from the waste receptacle. Filter 38 can be formed, for example, from an expanded polytetrafluoroethylene fibrous web or membrane. A drain opening 39 controlled by valves of conventional design (not shown) is provided for drainage of waste fluid 40 from the bottom of waste receptacle 35. Drainage may be accomplished by gravity flow. Vent opening 37 can be omitted in its entirety if opening 39 is of a size large enough to permit efficient venting of gases from receptacle 35.

Figure 5:
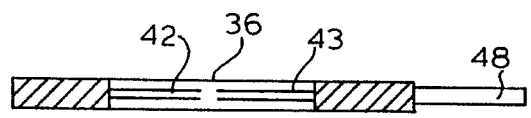
FIG. 5 is a cross-sectional side view of yet another alternative form of a top for the waste collection chamber of FIG. 3; and, FIG. 6 is a diagram in chart form illustrating a sequence of steps used to clean a probe in accordance with the invention.
Figure 4:
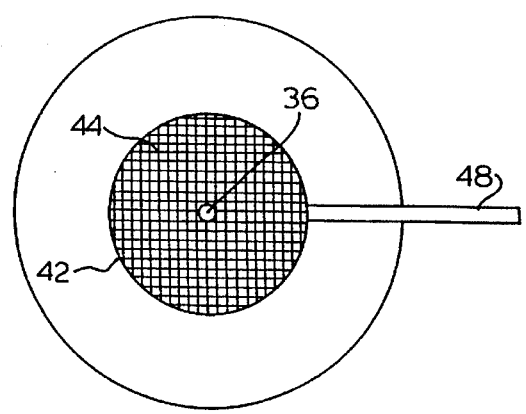
FIG. 4 is a top view of a waste collection chamber illustrating a different form of top closure.

The top of waste receptacle 35 is provided with a water-saturated closure 42, which performs the dual functions of cleaning the outside of probe 10 and preventing escape of aerosols. Closure 42 can, alternatively, be formed from bristles 43 (FIG. 5), a woven fabric 44 (FIG. 4), or non-woven fabric 45 (FIG. 3). Closure 42 is kept in a saturated condition by means of liquid 47 which is caused to flow through flow path 48 by means of a suitable pump 49. Fluid 47 is preferably water, but can, depending on the type of fluid being handled by probe 10, constitute or contain a disinfectant material.

In operation the effectiveness of the probe wash is enhanced by nearly simultaneous introduction of pressurized air and water which creates a turbulent flow. A segmented stream is created in flow path 24 by rapidly causing a burst of air to flow through the probe, followed by diluent liquid. The timing of the air flow to the probe, controlled by solenoid valve 30 or 31 is also such that flow path 24 will be filled with diluent liquid at the end of the wash cycle. The absence of air is critical to the normal system performance.

Figure 6:
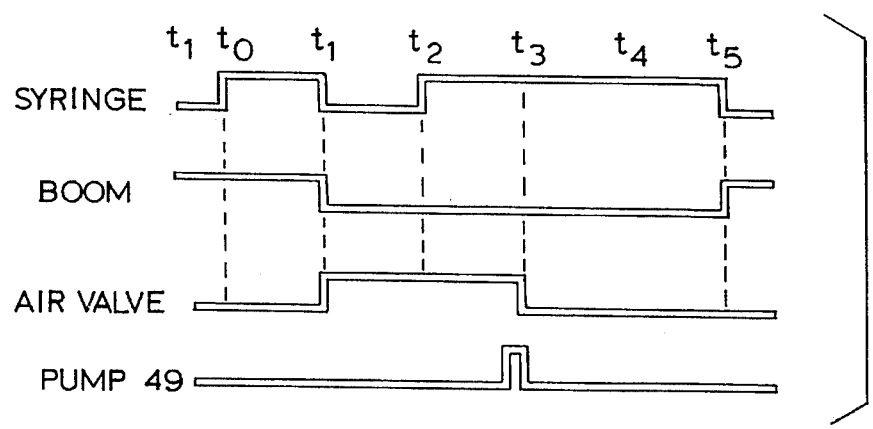

As illustrated in FIG. 6, a rapid, timed sequence of steps is used in the preferred backflushing procedure. In FIG. 6 the time intervals $t_{-1}$ to $t_0$, $t_0$ to $t_1$, $t_1$ to $t_2$, etc. are preferably in the range of 0.5 to 1.0 second. As seen in FIG. 6, at time $t_{-1}$ the boom 22 will lower the sample probe 10 into waste receptacle 35 so that the tip of the probe is roughly 0.4 inch into the waste receptacle. Then, at $t_0$ the syringe pump will charge flow path 24 with diluent. At time $t_1$ the air valve is activated to force air through the system thus forcing contaminated fluid out into waste receptacle 35. Pressurized air is vented out of the waste receptacle 35 through vent filter 38. At time $t_2$ the syringe will start to pump liquid through the system. At time $t_3$, the air pump will turn off, allowing fluid to be pumped through all legs of T-coupling 31. At time $t_3$ the solenoid valve turns off allowing the remaining liquid to flush any remaining air out of the tip of probe 10. At any time while the probe 10 is in waste receptacle 35 the pump 49 will flood closure 42 with liquid 47 to clean the exterior of probe tip 10. At $t_5$ the flow of diluent liquid is discontinued and the probe is raised out of the waste receptacle.

When the probe wash of this invention is used to clean a probe that is used to aspirate a liquid reagent rather than samples of liquids such as bodily fluids, it will be apparent that a stoppered tube would not be used as shown in the drawings. Rather the probe would be inserted into a suitable receptacle, which may have an open top, for aspiration of the desired reagent. The probe wash system of this invention is readily adapted to such applications.

The particular sequence or timing of wash steps also can be varied somewhat, as will be readily apparent to those skilled in the art. Modification of other aspects of the procedure may also be made without departing from the spirit of the invention.

What is claimed is:

1. Probe cleaning apparatus for a probe for aspirating successive aliquots of liquid from successive containers comprising:

a first fluid flow path connected to an upstream end of said probe which has an opposite distal tip, a source of diluent liquid connected to said first fluid flow path, means for pumping said diluent liquid into said first fluid flow path at controlled intervals, a source of pressurized gas connected by a second fluid flow path to the first fluid flow path at a point intermediate to the probe and the source of diluent liquid, valve means for controlling the flow of gas to said probe, whereby a segmented stream of said diluent liquid and said gas is introduced into said upstream end of said probe, is circulated through said probe, and is expelled through said tip of said probe for cleaning said probe, a waste receptacle having an opening at a top of said waste receptacle for receiving said probe during a cleaning cycle, wherein said opening is provided with a fibrous, air permeable material that surrounds said opening and is adapted to engage and clean the exterior of said probe, and means for moving said receptacle and said probe relative to each other whereby the probe is inserted through said opening during the cleaning cycle and removed therefrom during a liquid aliquot aspiration cycle.

2. Apparatus according to claim 1 wherein said gas comprises air.

3. Apparatus according to claim 1 in which said waste receptacle further includes an outlet for exhaust of gases therefrom, and means for moving said waste receptacle and said probe relative to each other whereby the probe is inserted through said opening during the cleaning cycle and removed therefrom during a liquid aliquot aspiration cycle.

4. Apparatus according to claim 1 further comprising means to supply a flow of liquid to said air permeable material to maintain said air permeable material in a saturated condition.

5. A method of cleaning a probe for aspirating successive aliquots of liquid from successive containers between aspiration of the successive aliquots comprising:

providing a first fluid flow path connected to an upstream end of said probe which has an opposite distal tip, providing a source of diluent liquid connected to said first fluid flow path, providing a source of pressurized gas connected by a second fluid flow path to the first fluid flow path at a point intermediate to the probe and the source of diluent liquid, valve means being provided in said flow path, introducing the tip of said probe into a waste receptacle comprising an opening, wherein a fibrous, air permeable material surrounds the opening to said water receptacle and engages and cleans the exterior of said probe, pumping said diluent liquid into said first fluid flow path after discharge from said probe of a liquid aliquot while maintaining said valve means in the closed position, stopping the pumping of said diluent and opening said valves means to cause pressurized gas to flow through said probe, resuming the pumping of said diluent while continuing the flow of said gas so as to create a segmented stream of said diluent liquid and said gas which flows through said probe and is expelled through said tip of said probe for cleaning said probe, closing said valve and maintaining the same in the closed position during the next liquid aliquot aspiration cycle, and discontinuing the flow of said diluent liquid.

6. A method according to claim 5 wherein the flow of diluent liquid is continued for a short time interval after said valve is closed thereby further washing the probe.

7. A method according to claim 5 wherein said gas comprises air.

8. A method according to claim 5 wherein said diluent liquid comprises water.

9. A method according to claim 5 wherein gases are caused to exit said receptacle through a filtered vent outlet.

10. A method according to claim 5 wherein a liquid is pumped to said fibrous, air permeable material to wet said fibrous, air permeable material, whereby the exterior of said probe is cleaned, and whereby the escape of aerosols from said receptacle is prevented.

11. A method of cleaning a probe between the steps of aspirating successive aliquots of liquid from successive containers comprising:

subsequent to discharge of an aliquot of liquid from a probe, introducing the tip of said probe into a vented waste receptacle comprising an opening, wherein a fibrous, air permeable material surrounds the opening to said waste receptacle and is adapted to engage and clean the exterior of said probe, expelling a diluent liquid through said probe, expelling a pressurized gas through said probe to form a turbulent, segmented flow of said liquid and said gas in said probe for cleaning said probe, discontinuing the flow of said gas while continuing to pump said diluent liquid into said probe, and withdrawing said probe from said receptacle.

12. A method according to claim 11 wherein said gas comprises air and said diluent liquid comprises water.

13. A method according to claim 11 wherein a liquid is pumped to said fibrous, air permeable material to wet said fibrous, air permeable material, whereby the exterior of said probe is cleaned, and whereby the escape of aerosols from said receptacle is prevented.

* * * * *